United States Patent
Hüglin et al.

(10) Patent No.: US 8,404,257 B1
(45) Date of Patent: *Mar. 26, 2013

(54) STABILISATION OF BODY-CARE AND HOUSEHOLD PRODUCTS

(75) Inventors: Dietmar Hüglin, Eimeldingen (DE); Thomas Ehlis, Freiburg (DE); Erich Kramer, Basel (CH); Joseph Anthony Lupia, Colfax, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/830,787

(22) PCT Filed: Oct. 21, 1999

(86) PCT No.: PCT/EP99/07981
§ 371 (c)(1),
(2), (4) Date: Sep. 4, 2001

(87) PCT Pub. No.: WO00/25731
PCT Pub. Date: May 11, 2000

Related U.S. Application Data

(60) Provisional application No. 60/106,634, filed on Nov. 2, 1998.

(51) Int. Cl.
*A61K 8/00* (2006.01)

(52) U.S. Cl. .............. 424/401; 424/59; 424/60; 424/61; 424/62; 424/64; 424/69; 424/70.1; 424/70.9

(58) Field of Classification Search .................. 424/401, 424/70.1, 59, 69; 514/458, 728
See application file for complete search history.

(56) References Cited

U.S. PATENT DOCUMENTS

| | | | |
|---|---|---|---|
| 3,356,612 A | 12/1967 | Gunthrie | |
| 4,806,580 A | 2/1989 | Bock et al. | 524/110 |
| 4,900,469 A | 2/1990 | Carty et al. | |
| 5,082,661 A * | 1/1992 | Melnik et al. | 424/401 |
| 5,106,891 A | 4/1992 | Valet | 524/91 |
| 5,175,312 A | 12/1992 | Dubs et al. | 549/307 |
| 5,242,689 A * | 9/1993 | Yoshihara et al. | 424/401 |
| 5,445,822 A * | 8/1995 | Bracco | 424/401 |
| 5,614,572 A | 3/1997 | Nesvadba et al. | |
| 5,688,995 A | 11/1997 | Luther et al. | |
| 5,716,918 A * | 2/1998 | Sivik et al. | 510/101 |
| 5,719,129 A * | 2/1998 | Andary et al. | 514/25 |
| 5,756,082 A * | 5/1998 | Cashin et al. | 424/78.03 |
| 5,789,373 A * | 8/1998 | Baker et al. | 510/522 |
| 6,042,839 A * | 3/2000 | Lahanas et al. | 424/401 |
| 6,090,370 A * | 7/2000 | Luther et al. | 424/59 |
| 6,117,997 A * | 9/2000 | Bulliard et al. | 544/216 |
| 6,184,375 B1 * | 2/2001 | Huglin et al. | 544/116 |
| 6,265,576 B1 * | 7/2001 | Gupta et al. | 544/216 |
| 6,284,821 B1 * | 9/2001 | Huglin et al. | 524/100 |

FOREIGN PATENT DOCUMENTS

| | | |
|---|---|---|
| DE | 19616570 | 10/1997 |
| EP | 0263524 | 4/1988 |
| EP | 0283252 | 9/1988 |
| EP | 0287342 | 10/1988 |
| EP | 0342483 | 11/1989 |
| EP | 0415887 | 3/1991 |
| EP | 0453396 | 10/1991 |
| GB | 1456199 | 11/1976 |
| GB | 2286774 | 8/1995 |
| GB | 2319523 A * | 5/1998 |
| WO | 94/07946 | 4/1994 |
| WO | 96/03481 | 2/1996 |
| WO | 97/27839 | 8/1997 |

OTHER PUBLICATIONS

Patent Abstracts of Japan, vol. 1998, No. 13, (1998) for JP 10204479.

* cited by examiner

*Primary Examiner* — Lakshmi Channavajjala
(74) *Attorney, Agent, or Firm* — Shiela A. Loggins; Tyler A. Stevenson

(57) ABSTRACT

A description is given of the use of phenolic antioxidants of formulae (1) and/or (2) and/or (3) for stabilizing body-care and household products.

12 Claims, No Drawings

STABILISATION OF BODY-CARE AND HOUSEHOLD PRODUCTS

This application is a 371 of PCT/EP 99/07981, filed Oct. 21, 1999, which claims priority of U.S. provisional app. No. 60/106,634, filed Nov. 2, 1998.

The present invention relates to the use of phenolic antioxidants for stabilising body-care and household products.

The product trend of recent years towards increasingly using natural substances based on oil and fat in cosmetic formulations and household products also increases the problem of the oxidative degradation of fats and oils, resulting in rancidity. Natural oils or unsaturated fatty acids are hardly ever absent from emulsions. Oxidative changes may sometimes produce reactive metabolites, for example ketones, aldehydes, acids, epoxides and lipoperoxides.

As a result there is on the one hand an undesirable change in the smell of the products and on the other hand substances may be obtained which may alter the skin tolerance. The un-controlled formation of free radicals on the skin contributes primarily to the initiation and progression of a multitude of pathophysical modulations, for example inflammation, cancerogenesis and the like.

However, oxidative degradation processes are not only found in the case of natural substances based on oil and fat. They are also found in a number of other cosmetic ingredients, such as fragrances and odoriferous substances, vitamins, colourants and the like.

To prevent oxidative degradation processes (photooxidation, autooxidation), so-called anti-oxidants (AO) are therefore used in cosmetic and food products. These antioxidants may be classified into compounds which prevent oxidation (complex formers, reducing agents and the like) and into compounds which interrupt the free radical chain reactions, for example butylated hydroxytoluene (BHT), butylated hydroxyanisol (BHA), gallates, such as propylgallate (PG), or t-butylhydroquinone (TBHQ). However, the latter compounds often do not meet the requirements with respect to pH stability as well as to light and temperature stability.

Surprisingly, it has been found that certain phenolic antioxidants meet these requirements.

Accordingly, this invention relates to the use of phenolic antioxidants of formula

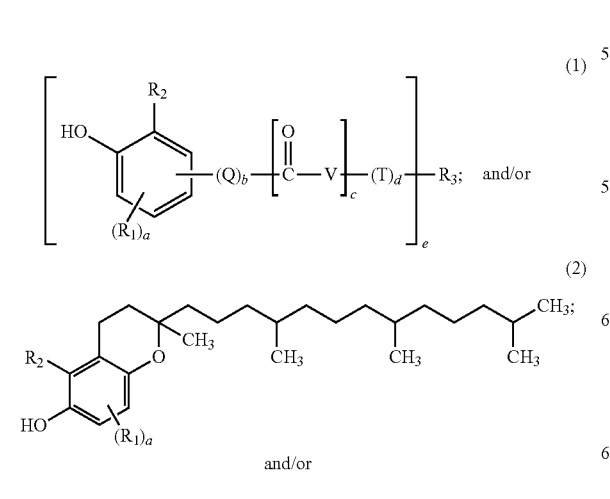

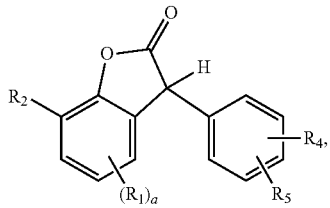

wherein in formulae (1), (2) and (3)
$R_1$ is hydrogen; $C_1$-$C_{22}$alkyl; $C_1$-$C_{22}$alkylthio; $C_5$-$C_7$cycloalkyl; phenyl; $C_7$-$C_9$-phenylalkyl; or $SO_3M$;
$R_2$ is $C_1$-$C_{22}$alkyl; $C_5$-$C_7$cycloalkyl; phenyl; or $C_7$-$C_9$-phenylalkyl;
Q is —$C_mH_{2m}$—;

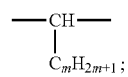

—$C_mH_{2m}$—NH; a radical of formula

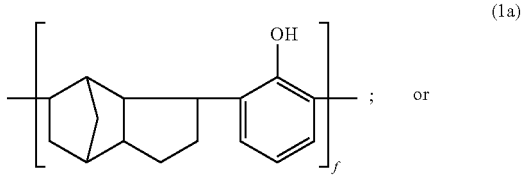

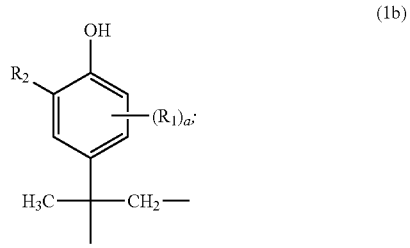

T is —$C_nH_{2n}$—; —$(CH_2)_n$—O—$CH_2$—;

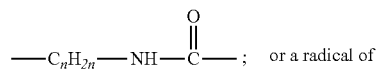

V is —O—; or —NH—;
a is 0; 1; or 2;
b, c and d are each independently of one another 0; or 1;
e is an integer from 1 to 4;
f is an integer from 1 to 3; and
m, n and p are each independently of one another an integer from 1 to 3;
if e=1, then
$R_3$ is hydrogen; M; $C_1$-$C_{22}$alkyl; $C_5$-$C_7$cycloalkyl; $C_1$-$C_{22}$alkylthio; $C_2$-$C_{18}$alkenyl; $C_1$-$C_{18}$ phenylalkyl; a radical of formula (1d)

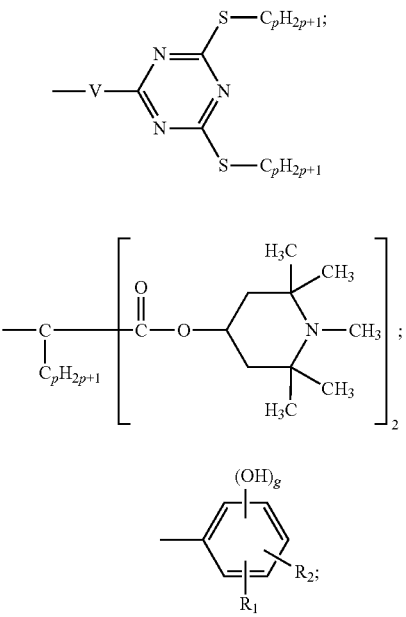

(1e)

M is alkali; ammonium;
if e=2, then
$R_3$ is a direct bond; —$CH_2$—;

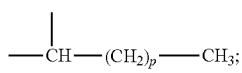

—O—; or —S—;
if
e=3, then $R_3$ is the radical of formula (1g)

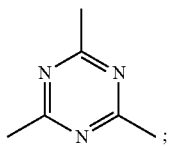

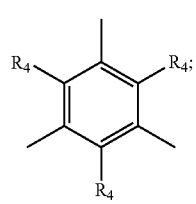

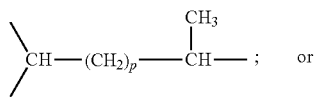

(1k)

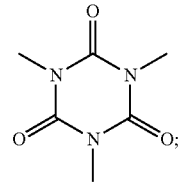

if
e=4, then $R_3$ is

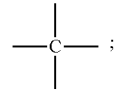

or a direct bond;

$R_4$ and $R_5$ are each independently of the other hydrogen; or $C_1$-$C_{22}$alkyl; for stabilising body-care and household products.

$C_1$-$C_{22}$Alkyl is straight-chain or branched alkyl radicals, such as methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_1$-$C_{22}$Alkylthio is straight-chain or branched alkylthio radicals, such as methylthio, ethylthio, n-propylthio, isopropylthio, n-butylthio, sec-butylthio, tert-butylthio, amylthio, heptylthio, octylthio, isooctylthio, nonylthio, decylthio, undecylthio, dodecylthio, tetradecylthio, pentadecylthio, hexadecylthio, heptadecylthio, octadecylthio or eicosylthio.

$C_2$-$C_{18}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_5$-$C_7$Cycloalkyl is cyclopentyl, cycloheptyl or, preferably, cyclohexyl.

$C_7$-$C_9$-Phenylalkyl is phenylpropyl, phenylethyl and, preferably, benzyl.

It is preferred to use antioxidants of formula (I), wherein Q is —$C_mH_{2m}$— and, preferably, a methylene or ethylene radical, and
m has the meaning given in formula (I).

V in formula (I) is preferably —O—.

Particularly interesting compounds of formula (I) are those, wherein
$R_1$ and $R_2$ are each independently of the other $C_1$-$C_{18}$alkyl and, in particular, $C_1$-$C_5$alkyl.

Other important compounds of formula (I) are those, wherein
a is 1.-

Very particularly interesting compounds are those of formula

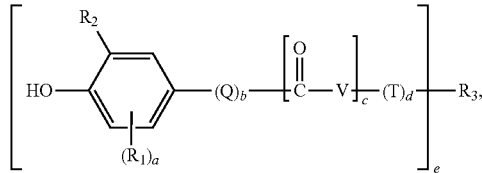
(2)

wherein $R_1$ and $R_2$ are each independently of the other $C_1$-$C_5$alkyl, a is 1 or 2; and $R_3$, Q, V, T, b, c, d and e have the meanings cited for formula (I).

Preferred compounds are those of formula (I), wherein $R_1$ and $R_2$ are the tert-butyl radical; and a is 1.

It is also preferred to use antioxidants of formula

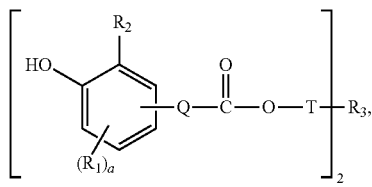
(3)

wherein $R_1$ and $R_2$ are each independently of the other $C_1$-$C_5$alkyl;

Q is —$C_mH_{2m}$—; or —$C_mH_{2m}$—NH—;

$R_3$ is a direct bond; —O—; —S—; —$CH_2$—; or

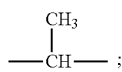

a is 1 or 2;

m is 1 to 5; and

T has the meaning cited in formula (I).

Interesting compounds of formula (I) are those, wherein

Q is ethylene; or

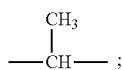

$R_3$ is a direct bond; and $R_1$, $R_2$, T and a have the meanings given in formula (3).

Likewise preferred are compounds of formula

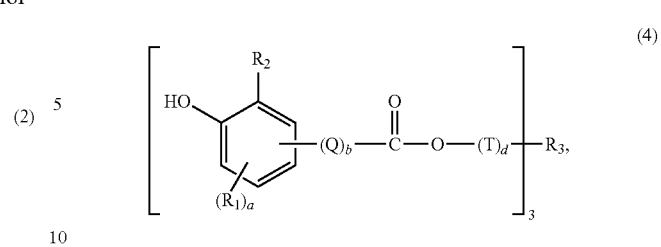
(4)

wherein

Q is —$C_mH_{2m}$—;

T is —$C_nH_{2n}$—;

$R_1$ and $R_2$ are each independently of the other $C_1$-$C_5$alkyl;

$R_3$ is the radical of formula (1g); (1 h); (1i); or (1k);

m and n are each independently of the other 1 to 3;

a is 1 or 2; and b and d are each independently of the other 0 or 1.

Other antioxidants which are preferably used conform to formula

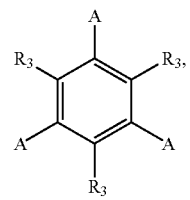
(5)

wherein

A is a radical of formula

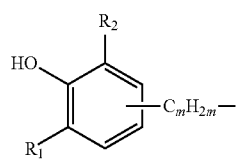
(5a)

$R_1$, $R_2$ and $R_3$ are each independently of one another $C_1$-$C_5$alkyl; and m is 1 to 3.

Other preferred antioxidants are those of formula

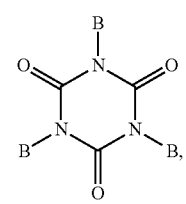
(6)

wherein

B is a radical of formula
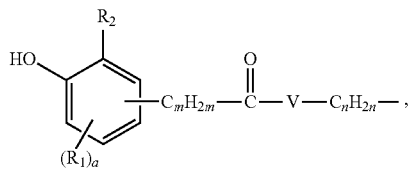
(6a)
$R_1$ and $R_2$ are each independently of the other $C_1$-$C_5$alkyl;
V is —O—; or —NH—;
a is 1; or 2;
m is 1 to 3; and
n is 0 to 3.
Examples of antioxidants used according to this invention are listed in Table 1:
TABLE 1
compound of formula
(7)
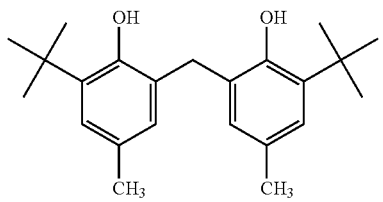 [SMILES: Cc1cc(Cc2cc(C)cc(C(C)(C)C)c2O)c(O)c(C(C)(C)C)c1]
(8)
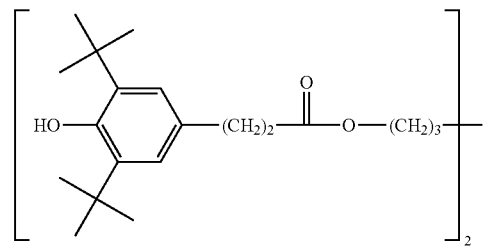
(9)
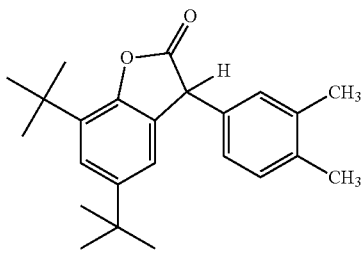 [SMILES: Cc1ccc(C2C(=O)Oc3c2cc(C(C)(C)C)cc3C(C)(C)C)cc1C]
(10)
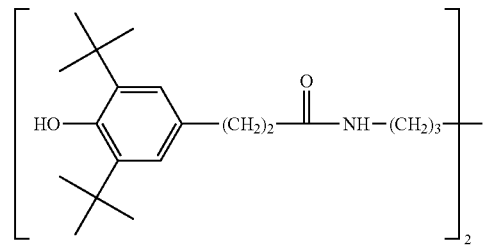
(11)
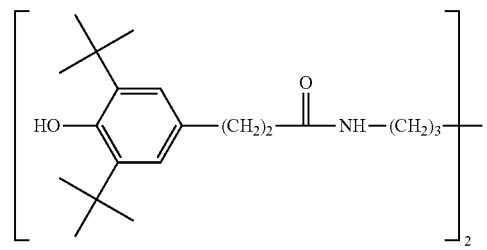

TABLE 1-continued
| compound of formula | |
|---|---|
| (12) | 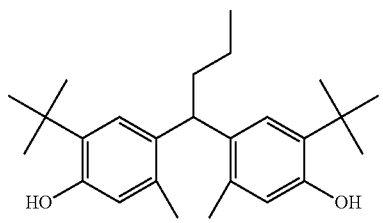 [SMILES: CCCC(c1cc(C(C)(C)C)c(O)cc1C)c1cc(C(C)(C)C)c(O)cc1C] |
| (13) | 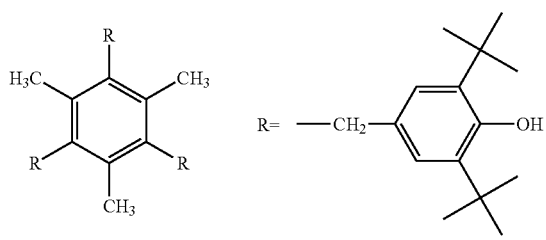 |
| (14) | 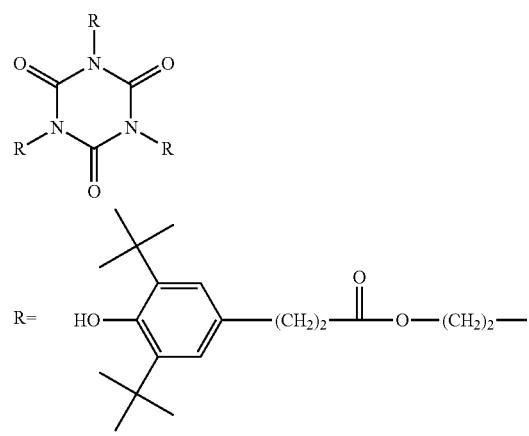 |
| (15) | 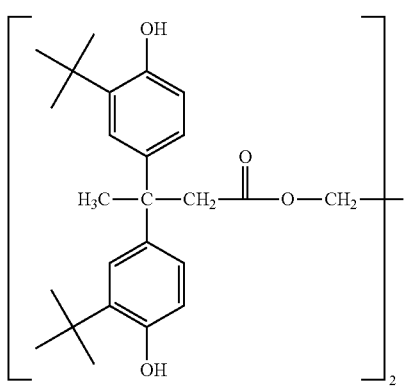 |
| (16) | 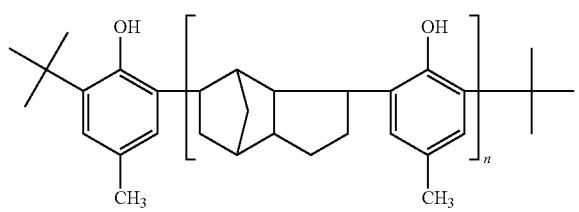 |
n = 1-3

TABLE 1-continued
| compound of formula | |
|---|---|
| (17) | 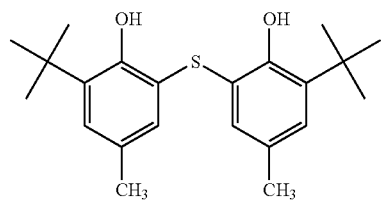 [SMILES: Cc1cc(Sc2cc(C)cc(C(C)(C)C)c2O)c(O)c(C(C)(C)C)c1] |
| (18) | 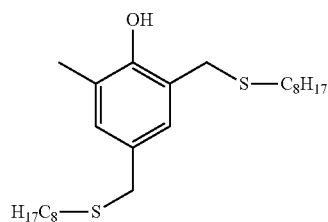 |
| (19) | 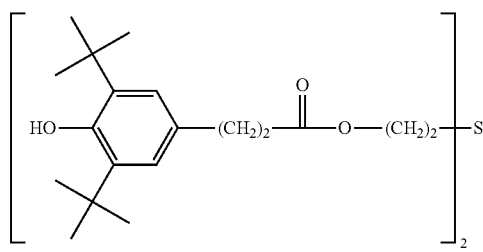 |
| (20) | 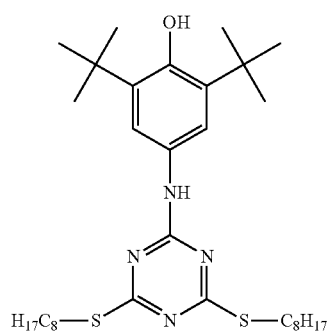 |
| (21) | 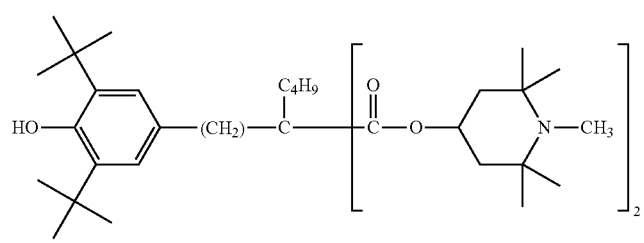 |
| (22) | 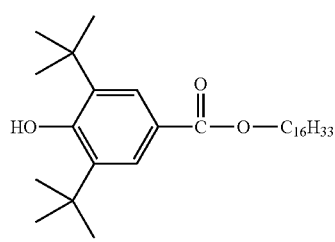 |

TABLE 1-continued
| compound of formula | |
|---|---|
| (23) | 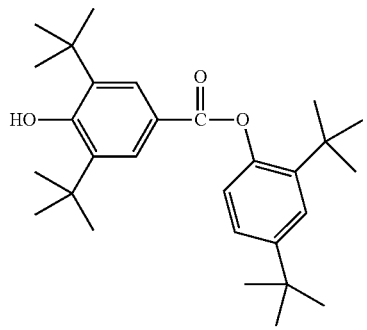 [SMILES: CC(C)(C)c1ccc(OC(=O)c2cc(C(C)(C)C)c(O)c(C(C)(C)C)c2)c(C(C)(C)C)c1] |
| (24) | 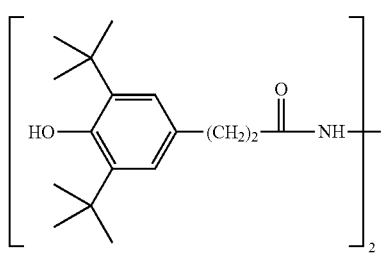 |
| (25) | 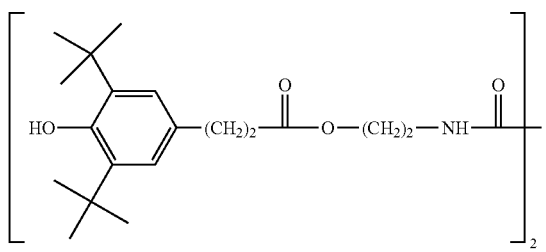 |
| (26) | 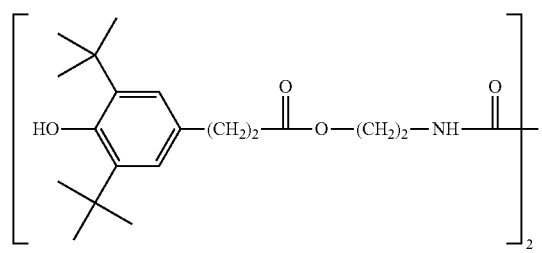 |
| (27) | 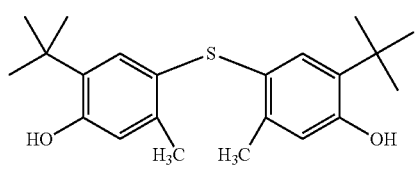 [SMILES: Cc1cc(O)c(C(C)(C)C)cc1Sc1cc(C(C)(C)C)c(O)cc1C] |
| (28) | 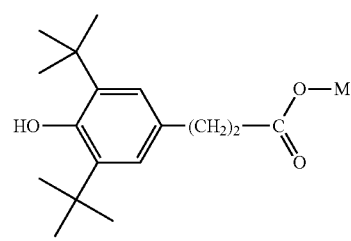 |
M = H, ammonium, alkali TABLE 1-continued

| compound of formula | |
|---|---|
| (29) | [structure: methylenebis(2-hydroxy-3,5-di-tert-butylphenyl) with CH bridge] |
| (30) | [structure: HO-(3,5-di-tert-butylphenyl)-(CH₂)₂-C(=O)-NH-C₆H₄-SO₃M]<br>M = H, Na |
| (31) | [HO-(3,5-di-tert-butylphenyl)-(CH₂)₂-C(=O)-O-CH₂-]₄C |
| (32) | HO-(3,5-di-tert-butylphenyl)-(CH₂)₂-C(=O)-O-C₁₈H₃₇ |
| (33) | [structure: tris(3,5-di-tert-butyl-4-hydroxybenzyl) substituted trimethylbenzene] |

The phenolic antioxidants of formulae (1), (2) and (3) can be used as individual compounds or as mixtures of several individual compounds.

The antioxidants used according to this invention have pronounced reactivity and can therefore be advantageously used at low temperatures. They furthermore have good hydrolytic stability, in particular in alkaline medium. Owing to their good solubility, they can be easily incorporated into the respective formulations.

The phenolic antioxidants of formulae (1), (2) and (3) can also be used together with tocopherol and/or tocopherol acetate.

The phenolic antioxidants of formulae (1), (2) and (3) can furthermore also be used together with light stabilisers.

Suitable light stabilisers are, for example, sterically hindered amines.

These include preferably a 2,2,6,6-tetraalkylpiperidine derivative containing at least one group of formula

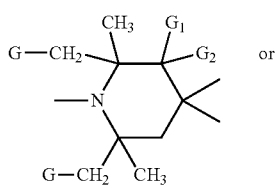
(34)

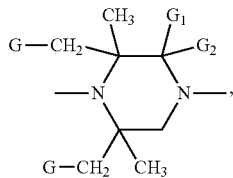
(35)

wherein G, $G_1$ and $G_2$ are each independently of one another hydrogen or methyl, preferably hydrogen.

Examples of tetraalkylpiperidine derivatives which can be used according to this invention are to be found in EP-A-356677, pages 3-17, paragraphs a) to f). The cited paragraphs of this EP-A are regarded as part of the present description. It is particularly useful to employ the following tetraalkylpiperidine derivatives:
bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, bis(1-octyloxy-2,2,6,6-tetramethylpiperidin-4-yl)sebacate, n-butyl-3,5-di-tert-butyl-4-hydroxybenzylmalonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetra methyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5] decane, the reaction product of 7,7,9,9-tetramethyl-2-cycloundecyl-1-oxa-3,8-diaza-4-oxospiro[4,5]decane and epichlorohydrin, tetra-(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro-[4,5]-decane-2,4-dione, or a compound of formulae

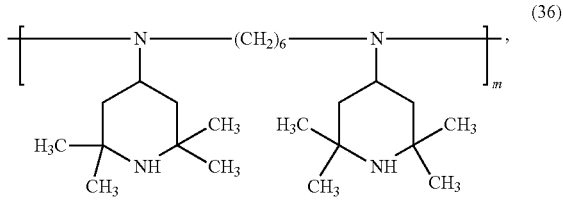
(36)

wherein m has a value of 5-50,

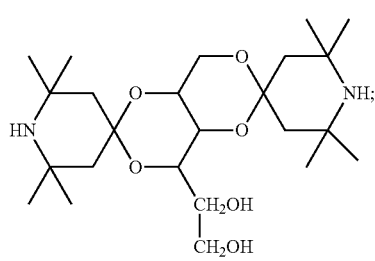
(37)

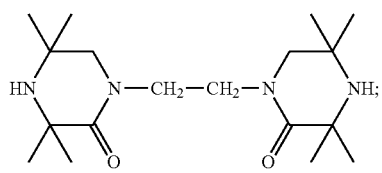
(38)

-continued

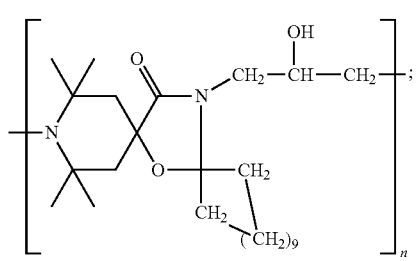

(39)

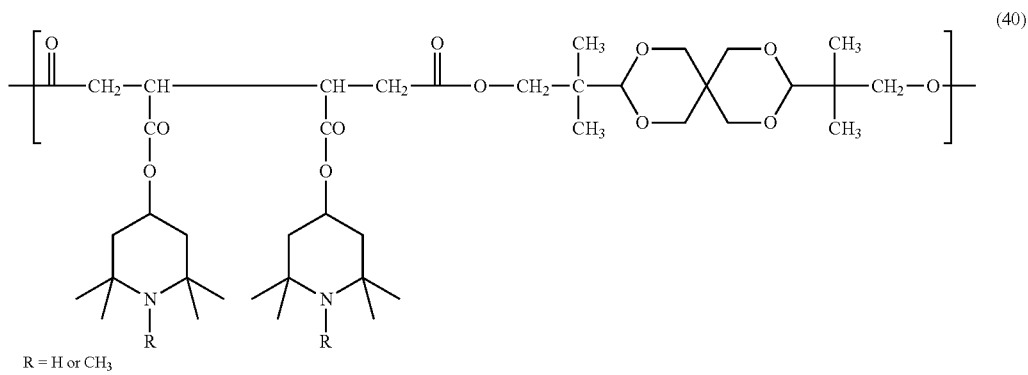

(40)

R = H or CH₃

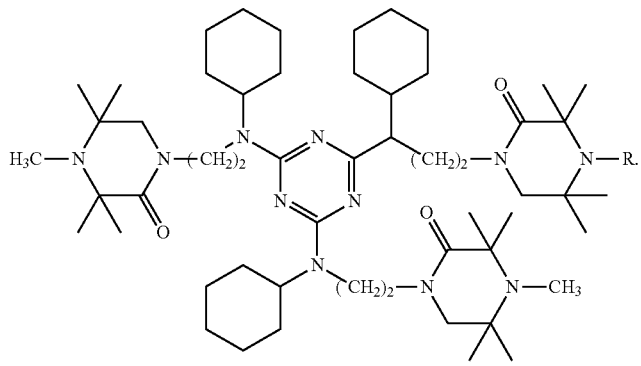

(41)

R=H or CH₃

It is also possible to use the inventive antioxidants of formulae (1), (2) and (3) together with benzotriazoles of formula

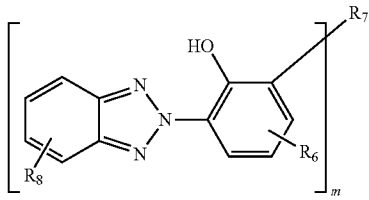

(42)

In formula (42), $R_6$ is $C_1$-$C_{12}$alkyl; $C_1$-$C_5$alkoxy; $C_1$-$C_5$alkoxycarbonyl; $C_5$-$C_7$cycloalkyl; $C_6$-$C_{10}$aryl; aralkyl; —SO₃M; a radical of formula (40a)

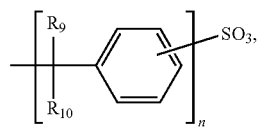

$R_8$ is hydrogen; $C_1$-$C_5$alkyl; $C_1$-$C_5$alkoxy; halogen, preferably Cl; or hydroxy $R_9$ and $R_{10}$ are each independently of the other hydrogen; or $C_1$-$C_5$alkyl;

m is 1 or 2;

n is 0 or 1;

if m=1, then $R_7$ is hydrogen; unsubstituted or phenyl-substituted $C_1$-$C_{12}$alkyl; $C_6$-$C_{10}$aryl;

A

B if m=2, then $R_7$ is a direct bond; —$(CH_2)_p$—; and p is 1 to 3.

The inventive antioxidants of formulae (1), (2) and (3) can also be used together with hydroxyphenyltriazine compounds of formula

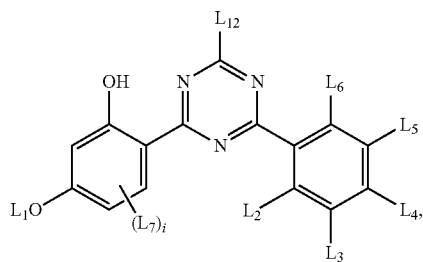

(43)

wherein $L_1$ is $C_1$-$C_{22}$alkyl, $C_2$-$C_{22}$alkenyl or $C_5$-$C_7$cycloalkyl;

$L_2$ and $L_6$ are each independently of the other H, OH, halogen, $C_1$-$C_{22}$alkyl, halomethyl;

$L_3$, $L_5$ and $L_7$ are each independently of one another H, OH, $OL_1$, halogen, $C_1$-$C_{22}$alkyl, halomethyl;

$L_4$ is H, OH, $OL_1$, halogen, $C_1$-$C_{22}$alkyl, phenyl, halomethyl;

$L_{12}$ is $C_1$-$C_{22}$alkyl, phenyl $C_1$-$C_5$alkyl, $C_5$-$C_7$cycloalkyl, $OL_1$ or, preferably a group of formula

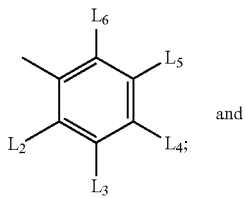

and j is 0, 1, 2 or 3.

If L-substituents are defined as alkyl or alkenyl, or if they are aromatic or aliphatic ring systems, then these contain within the scope of the cited meanings usually 1 to 50 carbon atoms and can be interrupted once or several times by O, S, NR', $SO_2$, CO, phenylene, cyclohexylene, COO, OCO, —$(SiR_pR_qO)$— and/or substituted once or several times by OH, OR', NR'R", halogen, —CN, alkenyl, phenyl, —$SiR_pR_qR_r$, or COOH, where R' and R" are each independently of the other H, alkyl, alkenyl or acyl, and $R_p$, $R_q$ and $R_r$ are each independently of the other H, alkyl, alkenyl, phenyl, alkoxy, acyl or acyloxy.

The above groups can also carry further substituents. Dimers or polymers are also possible.

Preferred 2-hydroxyphenyltriazines of this class are, for example, those of formulae

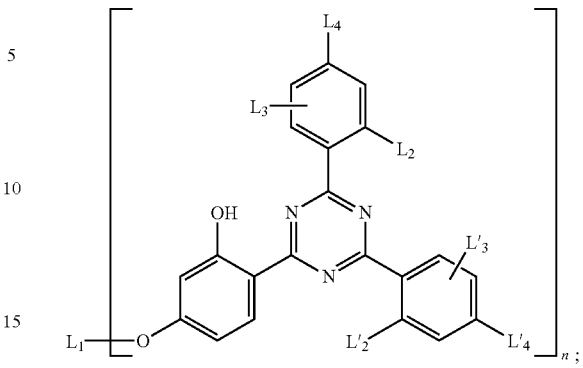

(44)

wherein in formula (44)

n is 1 or 2, and $L_1$, where n=1, is alkyl or alkyl which is interrupted by one or several O and/or substituted by one or several of the radicals OH, glycidyloxy, alkenoxy, COOH, $COOR^e$, O—CO—$R^f$; or alkenyl, cycloalkyl; phenylalkyl which is unsubstituted or substituted by OH, Cl or $CH_3$; $COR^g$; $SO_2$—$R^h$; $CH_2CH(OH)$—$R^j$; where $R^e$ is alkyl; alkenyl; hydroxyalkyl; alkyl or hydroxyalkyl which is interrupted by one or several O; cycloalkyl; benzyl; alkylphenyl; phenyl; phenylalkyl; furfuryl; or $CH_2CH(OH)$—$R^j$;

$R^f$, $R^g$ are each independently of the other alkyl, alkenyl or phenyl;

$R^h$ is alkyl, aryl or alkylaryl;

$R^j$ is aralkyl or $CH_2OR^k$;

$R^k$ is cyclohexyl, phenyl, tolyl, benzyl; and $L_1$, where n=2, is alkylene; alkenylene; xylylene; alkylene or hydroxyalkylene which is interrupted by one or several —O—; hydroxyalkylene;

$L_2$ and $L'_2$ are each independently of the other H, alkyl or OH;

$L_4$ and $L'_4$ are each independently of the other H, alkyl, OH, alkoxy, halogen and, where n=1, $OL_1$;

$L_3$ and $L'_3$ are each independently of the other H, alkyl or halogen.

$L_1$, $L_2$, $L'_2$, $L_3$, $L'_3$, $L_4$, $L'_4$ can within the scope of the cited meanings carry additional substituents, for example an ethylenically unsaturated polymerisable group. Dimers or polymers are also possible.

Examples of such compounds are, inter alia, 2,4,6-tris(2-hydroxy-4-octyloxyphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[2-hydroxy-4-(2-hydroxy-3-tridecyloxy-propyloxy)phenyl]-4,6-bis(2,4-dimethylphenyl)-1,3,5-triazine; and compounds of the following formulae:

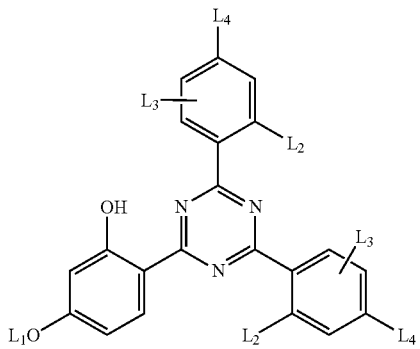

| compound of formula | $L_1$ | $L_2$ | $L_4$ | $L_3$ |
|---|---|---|---|---|
| (45) | CH₂CH(OH)CH₂O—CO—C(CH₃)=CH₂ | CH₃ | CH₃ | H |
| (46) | CH₂CH(OH)CH₂OC₁₂H₂₅/C₁₃H₂₇(mixture) | CH₃ | CH₃ | H |
| (47) | CH₂CH(OH)CH₂O—C₄H₉(n) | CH₃ | CH₃ | H |
| (48) | CH₂COO—C₁₈H₃₇ | H | H | m-CF₃ |
| (49) | C₈H₁₇ | CH₃ | CH₃ | H |
| (50) | CH₂CH(OH)CH(C₂H₅)—C₄H₉(n) | CH₃ | CH₃ | H |
| (51) | H | CH₃ | CH₃ | H |
| (52) | CH₂CH₂OH | H | H | H |
| (53) | C₈H₁₃ | H | H | H |
| (54) | C₁₈H₃₇ | CH₃ | CH₃ | o-CH₃ |
| (55) | CH₂CH(OH)CH₂O—C₄H₉(n) | H | H | H |
| (56) | CH(OH)—C₅H₁₁(n) | CH₃ | CH₃ | o-CH₃ |
| (57) | C₈H₁₇ | H | Cl | H |
| (58) | CH(CH₃)—COO—C₂H₅ | CH₃ | CH₃ | o-CH₃ |
| (59) | CH₂CH(OCOCH₃)CH(C₂H₅)—C₄H₉(n) | H | H | H |
| (60) | CH₂CH(OH)CH(C₂H₅)—C₄H₉(n) | H | H | H |
| (61) | CH₂CH₂—O—CO—C(CH₃)₃ | H | H | H |
| (62) | H | H | H | H |
| (63) | (CH₂)₁₀COO—C₂H₅ | H | Cl | H |
| (64) | (CH₂)₅COOH | H | H | H |
| (65) | CH₂CH(C₂H₅)—C₄H₉(n) | H | H | H |
| (66) | CH₂CH(OH)CH₂—O—C₄H₉(n) | H | H | t-C₄H₉H |
| (67) | CH₂CH(OH)CH₂—O—C₄H₉(n) | H | H | OCH₃H |
| (68) | (CH₂)₃—Si(CH₃)₃ | H | H | H |
| (69) | cyclohexyl | | | |
| (70) | CH₂CH(OH)CH₂—O-2-butyl/2-pentyl (mixture) | | | |
| (71) | CH₂CH(OH)CH₂—O—C₄H₉(n) | | | |
| (72) | (CH₂)₁₀COO—C₂H₅ | | | |
| (73) | C₄H₉ | | | |
| (74) | CH₂CH(OH)CH(C₂H₅)—C₄H₉(n) | | | |
| (75) | CH(C₃H₇)₂ | | | |
| (76) | cyclopentyl | | | |
| (77) | C(CH₃)₂—COO—C₂H₅ | | | |
| (78) | CH(CH₃)—COO—C₂H₅ | | | |
| (79) | (CH₂)₅—CH₃ | | | |
| (80) | CH₃ | | OCH₃ | |
| (81) | CH₂CH(OCOCH₃)CH(C₂H₅)—C₄H₉(n) | | OCH₂CH₂OC₂H₅ | |
| (82) | CH₂CH₂CH₂—O—CO—C₂H₅ | | OCH₃ | |
| (83) | CH₂CH(OH)CH₂—O—C₄H₉(n) | | CH₃ | |
| (84) | CH₂CH(OH)CH₂—O—C₄H₉(n) | | OCH₃ | |
| (85) | —CH₂—CH₂—CH(n-C₁₀H₂₁)(n-C₁₂H₂₅) | | | |
| (86) | iso-C₈H₃₈ | | | |
| (87) | —CH₂—CH₂—CH(n-C₆H₁₃)(n-Octyl) | | | |
| (88) | n-C₁₈H₃₇ | | | |
| (89) | 2-ethylhexyl | | | |

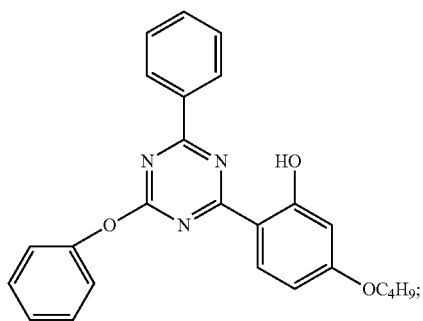
(90)

Abbreviations Used in the Above Formulae:

i=isomeric mixture; n=straight-chain radical; t=tertiary radical; o-, m-, p- designate the position of the radical relative to the triazine ring.

Examples of benzotriazole compounds which may be used in accordance with this invention:

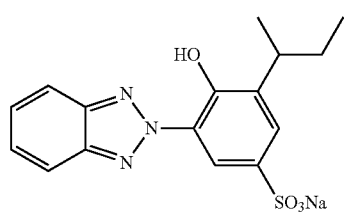
(91)

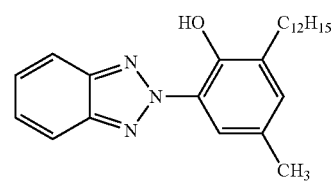
(92)

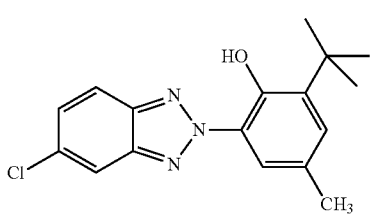
(93)

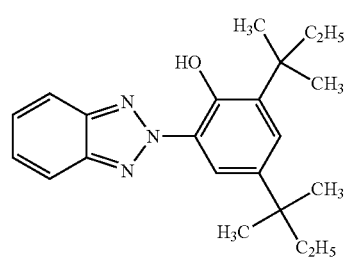
(94)

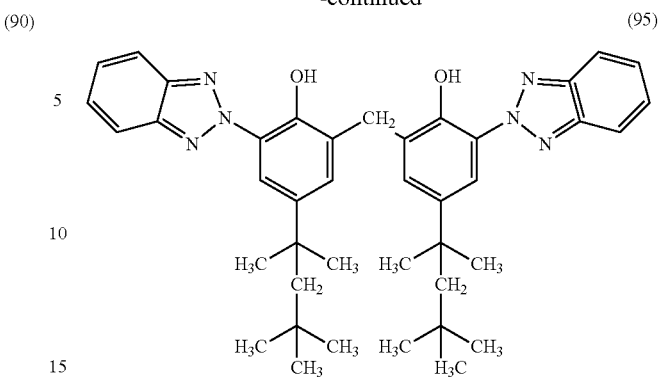
(95)

In addition, the inventive antioxidants of formulae (1), (2) and (3) can also be used together with complex formers, in particular nitrogen-containing complex formers, for example ethylenediaminetetracetic acid (EDTA), nitrilotriacetic acid (NTA), β-alaninediacetic acid (EDETA) or ethylenediaminedisuccinic acid (EDDS).

Other suitable complex formers conform to formula

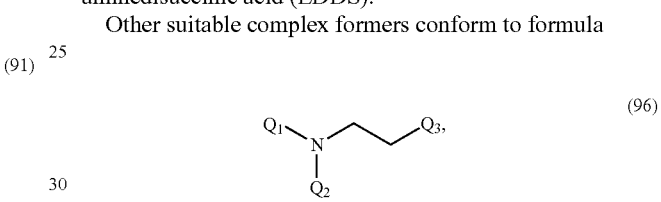
(96)

wherein $Q_1$, is $Carb_1$; $Carb_2$; or a radical of formula

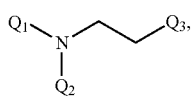

$Q_2$ is hydrogen or $Carb_2$; and
$Q_3$ is $Carb_3$; an amino acid radical; or a radical of formula

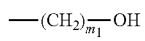
(96a)

wherein $Carb_1$, $Carb_2$ and $Carb_3$ are each independently of one another the radical of a $C_1$-$C_8$ mono- or dicarboxylic acid; and $m_1$ is 1 to 5.

Particularly preferred compounds are those of formula (96), wherein $Q_1$ is a monocarboxylic acid; or a radical of formula (96b)

$Q_2$ is hydrogen or a monocarboxylic acid; and
$Q_3$ is formula (96b); or a monocarboxylic acid.

Particularly interesting complex formers are those of formula (96), wherein $Carb_2$ and $Carb_3$ are each independently of the other the radical of formula (96c)—$[(CH_2)]_{n_1}$—COOH, wherein
$n_1$ is 0 to 5.

Complex formers which are important in practice are those conforming to formula

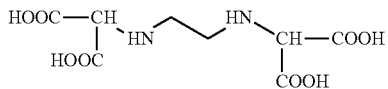 (97)

or to formula

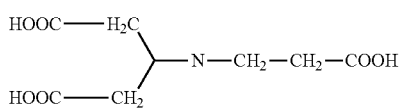 (98)

Nitrilotriacetic acid (NTA) is also suitable for use.

Other examples of complex formers which may be used according to this invention are aminetrimethylenephosphoric acid (ATMP) conforming to formula

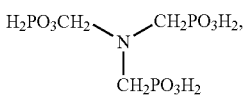 (99)

serinediacetic acid (SDA) conforming to formula

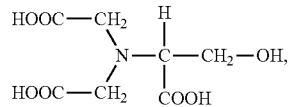 (100)

asparaginediacetic acid conforming to formula

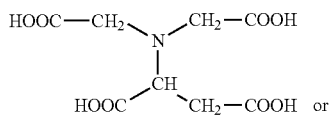 (101)

methylglycinediacetic acid (MGDA) conforming to formula

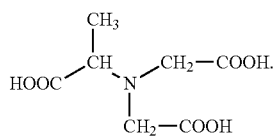 (102)

Other suitable complex formers are polyanionically-derived natural polysaccharides, for example containing phosphate, phosphonate or methylphosphonate groups, such as chitin derivatives, e.g. sulfochitin, carboxymethylchitin, phosphochitin, chitosan derivatives, for example sulfochitosan, carboxymethylchitosan or, very particularly preferably, phosphochitosan, which conform to formula

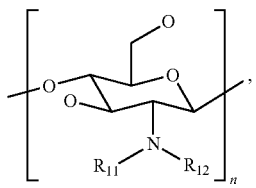 (103)

wherein
$R_{11}$ is hydrogen or a radical of formula

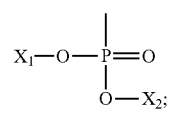 (103a)

$R_{12}$ is a radical of formula (1a);
$X_1$ and $X_2$ are each independently of the other hydrogen, $C_1$-$C_5$alkyl or an alkali ion or ammonium ion; and
n is 10 to 4000.

The antioxidants of formulae (1), (2) and (3) as well as mixtures of these compounds with light stabilisers or complex formers are particularly suitable for stabilising body-care products, in particular used for skin-care products, bath and shower additives, preparations containing fragrances and odoriferous substances, hair-care products, dentifrices, deodorising and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturising gels, moisturising sprays, revitalising body sprays, cellulite gels and peeling preparations.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The cited body-care products can be in the form of creams, ointments, pastes, foams, gels, lotions, powders, make-ups, sprays, sticks or aerosols. They preferably contain the antioxidants of formulae (1) and/or (2) and/or (3) and, optionally, the above light stabilisers in the oil phase or in the aqueous or aqueous/alcoholic phase.

This invention therefore also relates to a body-care product containing at least one phenolic antioxidant of formula (1) and/or (2) and/or (3).

The antioxidant(s) are usually present in the novel body-care product in a concentration of 50 to 1000 ppm.

Creams are oil-in-water emulsions containing more than 50% of water. The oil-containing base used therein is usually mainly fatty alcohols, for example lauryl, cetyl or stearyl alcohol, fatty acids, for example palmitic or stearic acid, liquid to solid waxes, for example isopropylmyristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty acid ether (Tween trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, preferably not more than 20 to 50%, of water or of an aqueous phase. The oil-containing phase contains predominantly hydrocarbons, such as paraffin oil and/or solid paraffin which preferably contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturisers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or, preferably, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum arabic. The gels preferably additionally contain also polyalcohols, such as propylene glycol or glycerol as moisturisers and wetting agents, such as polyoxyethylenesobitan fatty acid ester. The gels furthermore contain commercially available preservatives, such as benzyl alcohol, phenethyl alcohol, phenoxyethanol and the like.

The following Table lists typical examples of body-care products of this invention and their ingredients:

| Body-care product | Ingredients |
| --- | --- |
| moisturising cream | vegetable oil, emulsifier, thickener, perfume, water, antioxidant |
| shampoo | surfactant, emulsifier, preservatives, perfume, antioxidant |
| toothpaste | cleaning agent, thickener, sweetener, flavour, colourant, antioxidant, water |
| lip-care stick | vegetable oil, wax, $TiO_2$, antioxidant |

The novel body-care products have high stability towards colour changes and chemical degradation of the ingredients present in these products. This is to be attributed to the effectiveness, colour stability, ease of incorporation and hydrolytic stability of the antioxidants used.

The phenolic antioxidants are also used in household cleaning and treatment agents, for example in liquid scouring agents, glass detergents, neutral cleaners (all-purpose cleaners), acid household cleaners (bath), WC cleaners, preferably in washing, rinsing and dishwashing agents, clear rinsing agents, dishwasher detergents, shoe polishes, polishing waxes, floor detergents and polishes, metal, glass and ceramic cleaners, textile-care agents, agents for removing rust, colour and stains (stain remover salt), furniture and multipurpose polishes and leather dressing agents (leather sprays).

Typical examples of novel household cleaning and treating agents are:

| Household cleaners/household treating agents | Ingredients |
| --- | --- |
| detergent concentrate | surfactant mixture, ethanol, antioxidant, water |
| shoe polish | wax, wax emulsifier, antioxidant, water, preservative |
| wax-containing floor cleaning agent | emulsifier, wax, sodium chloride, antioxidant, water, preservative |

The antioxidant(s) are usually incorporated by dissolution in an oil phase or alcoholic or water phase, where required at elevated temperature. Details can be found in the Examples.

The phenolic antioxidants of formulae (1), (2) and (3) also have pronounced antimicrobial action.

The following Examples illustrate the invention.

PREPARATION OF STABILISED FORMULATIONS OF BODY-CARE PRODUCTS

Example 1A

Preparation of a Moisturiser Cream

| Phase | Ingredients | (w/w) % |
| --- | --- | --- |
| A | passionflower oil | 8 |
|   | glyceryl dioleate | 4 |
|   | dicapryl ether | 4 |
|   | isopropylisostearate | 4 |
|   | antioxidant of formula (31) | 0.05 |
| B | water, demin. | ad. 100 |
|   | EDTA | 0.1 |
| C | carbomer | 0.15 |
| D | sodium hydroxide | 10% |
|   |   | 0.20 |
| E | perfume; preservative | q.s. |

Preparation:

The components (A) are thoroughly mixed in a homogeniser for 10 min at 75-80° C. The water (B), likewise heated to 75-80° C. beforehand, is slowly added and the mixture is homogenised for 1 min. The mixture is cooled, with stirring, to 40° C. and then (C) and (E) are added and the mixture is homogenised for 1 min. Subsequently, (D) is added and the mixture is homogenised for ½ min and cooled, with stirring, to room temperature.

Alternatively to the antioxidant of the formulae (31) the following antioxidants can be applied (0.05%):

Example 1b: antioxidant of the formula (7)
Example 1c: antioxidant of the formula (32)
Example 1d: antioxidant of the formula (33)

Example 2

Preparation of a Toilet Water (w/w) %

| Ingredients | (w/w) % |
| --- | --- |
| ethanol, 96% | 60 |
| d-limonene | 5 |
| cedrene | 1.5 |
| citronellol | 0.5 |
| savin | 0.5 |
| antioxidant of formula (29) | 0.08 |
| UV absorber of formula (91) | 0.1 |
| S,S-EDDS | 0.005 |
| colourant (D&C Yellow No. 5) | 0.02 |
| water | ad. 100 |

Preparation:

The components are thoroughly mixed in the cited sequence at 50° C., a clear homogeneous solution being obtained.

Example 3

Preparation of a Hair Styling Spray

| Ingredients | (w/w) % |
| --- | --- |
| alcohol, anhydrous | 96.21 |
| octylacrylamide/acrylate/butylaminoethylmethacrylate copolymer | 2.52 |
| hydroxypropyl cellulose | 0.51 |
| aminomethylpropanol (95%) | 0.46 |
| antioxidant of formula (33) | 0.05 |
| benzophenone-4 | 0.05 |
| perfume oil | 0.20 |

Preparation:

The hydroxypropyl cellulose is first predissolved in half of the alcohol (Vortex mixer) and is charged with the aminomethylpropanol. The other components—with the exception of the acrylate resin—are dissolved in alcohol and this solution is added, with stirring, to the hydroxypropyl cellulose. Subsequently, the acrylate resin is added and stirred until completely dissolved.

Example 4

Preparation of a Shampoo for Greasy Hair

| Ingredients | (w/w) % |
| --- | --- |
| sodium myreth sulfate | 50.00 |
| TEA abietoyl collagen hydrolysate | 3.50 |
| laureth-3 | 3.00 |
| colourant (D&C Red No. 33) | 0.20 |
| antioxidant of formula (29) | 0.05 |
| UV absorber of formula (92) | 0.15 |
| phosphonomethylchitosan, sodium salt | 0.01 |
| perfume oil | 0.10 |
| water | ad. 100 |

Preparation:

The components are mixed, with stirring, at room temperature until they are completely dissolved. The pH is 6.5.

Preparation of Stabilised Household Products

| Ingredients | (w/w) % |
| --- | --- |
| synthetic soap (Zetesap 813) | 7.85 |
| glycerol | 6.00 |
| anionic surfactant (Lumorol 4192; Mulsifan RT 13) | 22.00 |
| Vaseline | 11.00 |
| paraffin 52/54 | 20.00 |
| talcum | 2.00 |
| orange terpene | 4.00 |
| antioxidant of formula (33) | 0.02 |
| water | 27.13 |

Preparation:

The antioxidant is predissolved in the terpene. The components are then stirred in the cited sequence at about 65° C. until homogeneous. The mixture is then cooled to room temperature.

Example 6

Preparation of a Glass Detergent

| Ingredients | (w/w) % |
| --- | --- |
| anionic/amphoteric surfactants (Lumorol RK) | 0.7 |
| butyl glycol | 5.0 |
| isopropanol | 20.0 |
| d-limonene | 4.00 |
| antioxidant of formula (32) | 0.02 |
| water, demin. | ad. 100 |

Preparation:

The antioxidant is predissolved in the terpene. The components are then dissolved in the cited sequence until a clear homogeneous mixture is obtained.

What is claimed is:

1. A method of preventing photooxidation and autooxidation processes in body-care products selected from body oils, body lotions and body gels, which method comprises incorporating by dissolution in an oil phase or alcoholic or water phase, into said body-care products one or more phenolic antioxidants of formula (1)

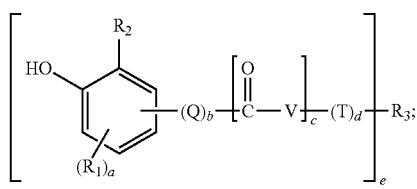

(1)

wherein $R_1$ is a tert-butyl radical or is $C_1$-$C_{22}$alkyl and
$R_2$ is tert-butyl radical;
Q is a radical of formula

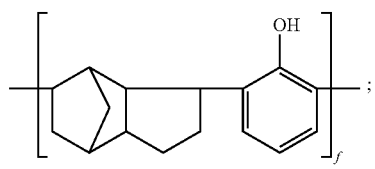

(1a)

T is —$C_nH_{2n}$—;
a is 0, 1 or 2;
b is 1;
d is 0 or 1;
e is an integer from 1 to 3;
f is an integer from 1 to 3;
m, n and p are each independently of one another an integer from 1 to 3;
if e=1, then
$R_3$ is; $C_1$-$C_{22}$alkyl or (1f)

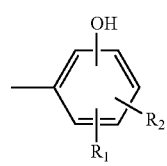

if e=2, then
$R_3$ is a direct bond, —$CH_2$—, S or

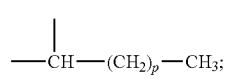

and
if e=3, then
$R_3$ is the radical of formula

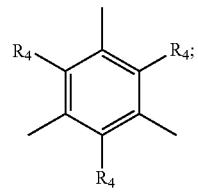

(1h)

c is 0;
where the antioxidants are incorporated in a concentration of 50 to 1000 ppm, with the proviso that the body-care product contains an aqueous or aqueous/alcoholic phase.

2. A method according to claim 1,
wherein
$R_1$ and $R_2$ are the tert-butyl radical;
$R_3$ is a direct bond;
m is 1 to 3;
d is 0 and
e is 2.

3. A method according to claim 1, which comprises incorporating the phenolic antioxidants of formula (I) as individual compounds or as a mixture of several individual compounds.

4. The method according to claim 1 which body care product further comprises tocopherol and/or tocopherol acetate.

5. The method according to claim 1, which body care product further comprises light stabilisers.

6. The method according to claim 5, wherein the light stabilisers are sterically hindered amines.

7. The method according to claim 5, wherein the light stabilisers used are benzotriazoles of formula

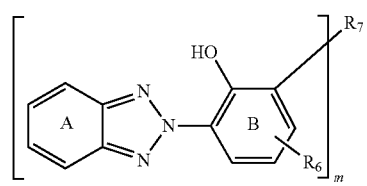

40(40)

wherein
$R_6$ is $C_1$-$C_{12}$alkyl; $C_1$-$C_5$alkoxy; $C_1$-$C_5$alkoxycarbonyl; $C_5$-$C_7$cycloalkyl; $C_6$-$C_{10}$aryl; aralkyl; —$SO_3M$; a radical of formula ( . . . a)

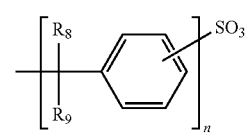

$R_8$ and $R_9$ are each independently of the other hydrogen; or $C_1$-$C_5$alkyl;
m is 1 or 2;
n is 0 or 1;
if m=1,
$R_7$ is hydrogen; unsubstituted or phenyl-substituted $C_1$-$C_{12}$alkyl; $C_6$-$C_{10}$aryl;
if n=2,
$R_2$ is a direct bond; —$(CH_2)_p$—; and
p is 1 to 3.

8. The method according to claim 5, wherein the light stabilisers are 2-hydroxyphenyltriazines of formula

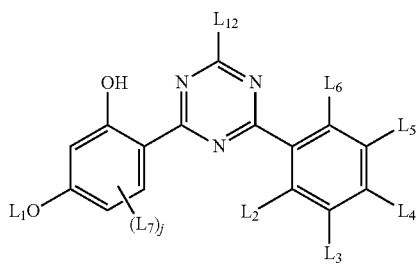
(41)

wherein
$L_1$ is $C_1$-$C_{22}$alkyl, $C_2$-$C_{22}$alkenyl or $C_5$-$C_7$cycloalkyl;
$L_2$ and $L_6$ are each independently of the other H, OH, halogen, $C_1$-$C_{22}$alkyl, halomethyl;
$L_3$, $L_5$ and $L_7$ are each independently of one another H, OH, $OL_1$, halogen, $C_1$-$C_{22}$alkyl, halomethyl;
$L_4$ is H, OH, $OL_1$, halogen, $C_1$-$C_{22}$alkyl, phenyl, halomethyl;
$L_{12}$ is $C_1$-$C_{22}$alkyl, phenyl $C_1$-$C_5$alkyl, $C_5$-$C_7$cycloalkyl, $OL_1$ or, preferably, a group of formula

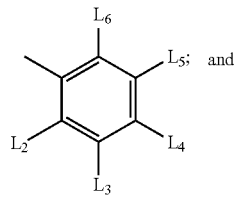

j is 0, 1, 2 or 3.

9. The method according to claim 1, wherein the body-care products are for the skin and its adnexa.

10. The method according to claim 1, wherein the body-care products are selected from skin-care products, bath and shower additives, preparations containing fragrances and odoriferous substances, hair-care products, dentifrices, deodorising and antiperspirant preparations, decorative preparations, light protection formulations and preparations containing active ingredients.

11. The method according to claim 1, wherein the body care product further contains fragrances, olfactory substances and/or an oil selected from group consisting of fatty alcohols, fatty acids and liquid to solid waxes.

12. the method according to claim 1, wherein the phenolic antioxidant of formula 1 is selected from the group consisting of

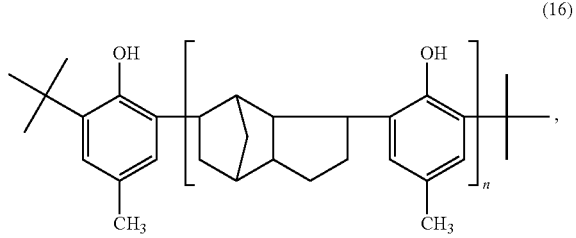
(16)

n = 1-3.

* * * * *